(12) United States Patent
Breindel

(10) Patent No.: US 10,251,662 B2
(45) Date of Patent: Apr. 9, 2019

(54) SURGICAL INSTRUMENTS FOR BLUNT AND SHARP TISSUE DISSECTION

(71) Applicant: Covidien LP, Mansfield, MA (US)

(72) Inventor: Jay T. Breindel, Kensington, CT (US)

(73) Assignee: Covidien LP, Mansfield, MA (US)

( * ) Notice: Subject to any disclaimer, the term of this patent is extended or adjusted under 35 U.S.C. 154(b) by 298 days.

(21) Appl. No.: 15/156,710

(22) Filed: May 17, 2016

(65) Prior Publication Data

US 2016/0354102 A1 Dec. 8, 2016

Related U.S. Application Data

(60) Provisional application No. 62/170,907, filed on Jun. 4, 2015.

(51) Int. Cl.
| | |
|---|---|
| *A61B 17/32* | (2006.01) |
| *A61B 17/285* | (2006.01) |
| *A61B 17/295* | (2006.01) |
| *A61B 17/3201* | (2006.01) |
| *A61B 17/00* | (2006.01) |

(52) U.S. Cl.
CPC ........... *A61B 17/32* (2013.01); *A61B 17/285* (2013.01); *A61B 17/295* (2013.01); *A61B 17/3201* (2013.01); *A61B 2017/00557* (2013.01); *A61B 2017/320044* (2013.01); *A61B 2017/320048* (2013.01)

(58) Field of Classification Search
CPC ..... A61B 17/285; A61B 17/295; A61B 17/32; A61B 2017/00557; A61B 2017/320044
See application file for complete search history.

(56) References Cited

U.S. PATENT DOCUMENTS

| | | |
|---|---|---|
| 6,293,952 B1 | 9/2001 | Brosens et al. |
| 6,758,853 B2 | 7/2004 | Kieturakis et al. |
| 6,808,492 B2 | 10/2004 | Snyder |
| 7,300,448 B2 | 11/2007 | Criscuolo et al. |
| 7,695,487 B2 | 4/2010 | Peartree et al. |
| 8,360,950 B2 | 1/2013 | Acosta et al. |
| 8,540,745 B2 | 9/2013 | Criscuolo et al. |
| 2006/0167482 A1 | 7/2006 | Swain et al. |
| 2009/0312783 A1 | 12/2009 | Whayne et al. |
| 2011/0160539 A1* | 6/2011 | Robertson .......... A61B 17/3421 600/204 |
| 2014/0276790 A1* | 9/2014 | Raybin ............... A61B 18/1492 606/41 |

FOREIGN PATENT DOCUMENTS

WO 2006031934 A2 3/2006

OTHER PUBLICATIONS

European Search Report dated Jul. 26, 2016, issued in European Application No. 16172840.

* cited by examiner

*Primary Examiner* — Julie A Szpira

(57) ABSTRACT

A surgical instrument including a housing, an elongated body, an end effector, and a dissection element. The housing has a handle assembly and the elongated body extends from the housing. The end effector is supported at a distal end of the elongated body and is operatively associated with the handle assembly. The dissection element is disposed about the elongated body proximal to the distal end of the elongated body. The dissection element is configured to bluntly dissect tissue surrounding the elongated body.

20 Claims, 5 Drawing Sheets

SURGICAL INSTRUMENTS FOR BLUNT AND SHARP TISSUE DISSECTION

CROSS-REFERENCE TO RELATED APPLICATIONS

This application claims the benefit of and priority to U.S. Provisional Patent Application No. 62/170,907 filed Jun. 4, 2015, the entire disclosure of which is incorporated by reference herein.

BACKGROUND

1. Technical Field

The present disclosure relates to surgical instruments and, more specifically, to surgical instruments having both a blunt and sharp tissue dissection capability.

2. Discussion of Related Art

During endoscopic surgical procedures, surgical instrumentation is inserted through a small incision or incisions to access a surgical site. Typically, during endoscopic surgical procedures tissue adjacent the surgical site must be dissected to accommodate the surgical instrumentation and provide space to facilitate manipulation of tissue being treated.

Depending on the type of tissue to be dissected, it is known to perform blunt tissue dissection (dissection of tissue along existing seams or natural planes), e.g., balloon dissection, and sharp dissection (cutting of seamless tissue), e.g., dissection with scissor-type dissectors, scalpels, etc.

In some procedures both blunt tissue dissectors and sharp tissue dissectors are required to define the space adjacent the surgical site. In these procedures, it is necessary to remove one dissector and insert a second dissector through the incision to perform the surgical procedure. This requirement of multiple instruments increases the time required to perform the procedure.

Accordingly, there is a continuing need for dissection instruments suitable for use during endoscopic procedures that reduce the time of the procedure and reduce the cost of such procedures.

SUMMARY

In an aspect of the present disclosure, a surgical instrument includes a housing, an elongated body, an end effector, and a dissection element. The housing has a handle assembly. The elongated body extends from the housing. The end effector is supported at a distal end of the elongated body. The end effector is operably associated with the handle assembly. The dissection element is disposed about the elongated body proximal to the distal end of the elongated body. The dissection element is configured to bluntly dissect tissue surrounding the elongated body. The dissection element may be a balloon.

In aspects, the dissection element includes a proximal cuff, a distal cuff, and a dissection wall between the proximal and distal cuffs. The distal cuff may be disposed about the elongated body and is adjacent the distal end of the elongated body. The proximal cuff may be disposed about the elongated body and is proximal to the distal cuff. The proximal or distal cuff may be longitudinally fixed to the elongated body. The dissection element may have an expanded configuration such that the dissection wall of the dissection element is arcuate between the proximal and distal cuffs.

In some aspects, the dissection element has a contracted configuration such that a dissection wall of the dissection element is substantially linear. In the contracted configuration the dissection wall may be substantially parallel to a longitudinal axis of the elongated body and may be coplanar with an outer wall of the elongated body.

In certain aspects, the housing includes an inflation port that is in fluid communication with an interior of the dissection element. An outer wall of the elongated body may define an inflation channel and an inflation opening that fluidly connects to the inflation port and the interior of the dissection element. The instrument may include a drive rod that passes through the inflation channel of the elongated body to operably couple to the handle assembly to the end effector. The elongated body may include a proximal seal and a distal seal that are positioned about the drive rod to seal the inflation channel. The proximal seal may be positioned proximal to the inflation port and the distal seal may be positioned distal to the inflation openings. The inflation port may include a release valve that I configured to release inflation fluid from the interior of the dissection element.

In particular aspects, the end effector includes a first jaw member and a second jaw member that are moveable relative to one another. The first and/or second jaw member may define a sharp tissue dissector. The first and second jaw members may include a grasping and cutting function.

In another aspect of the present disclosure, a method includes inserting a surgical instrument through an opening in a body cavity of a patient to access a surgical site, positioning a dissection element of the surgical instrument adjacent tissue to be dissected, expanding the dissection element to bluntly dissect tissue adjacent the surgical instrument, contracting the dissection element, and treating targeted tissue with an end effector of the surgical instrument positioned distal to the dissection element.

In aspects, treating the targeted tissue with the end effector includes sharp dissection of the targeted tissue. Expanding the dissection element may include injecting fluid through an injection port disposed on a housing of the surgical instrument such that the fluid increased pressure within an interior of the dissection element. Contracting the dissection element may include removing fluid through the injection port such that the fluid decreases pressure within an interior of the dissection element. Contracting the direction element may include opening a release valve of the injection port such that pressure within the interior of the dissection element is released.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
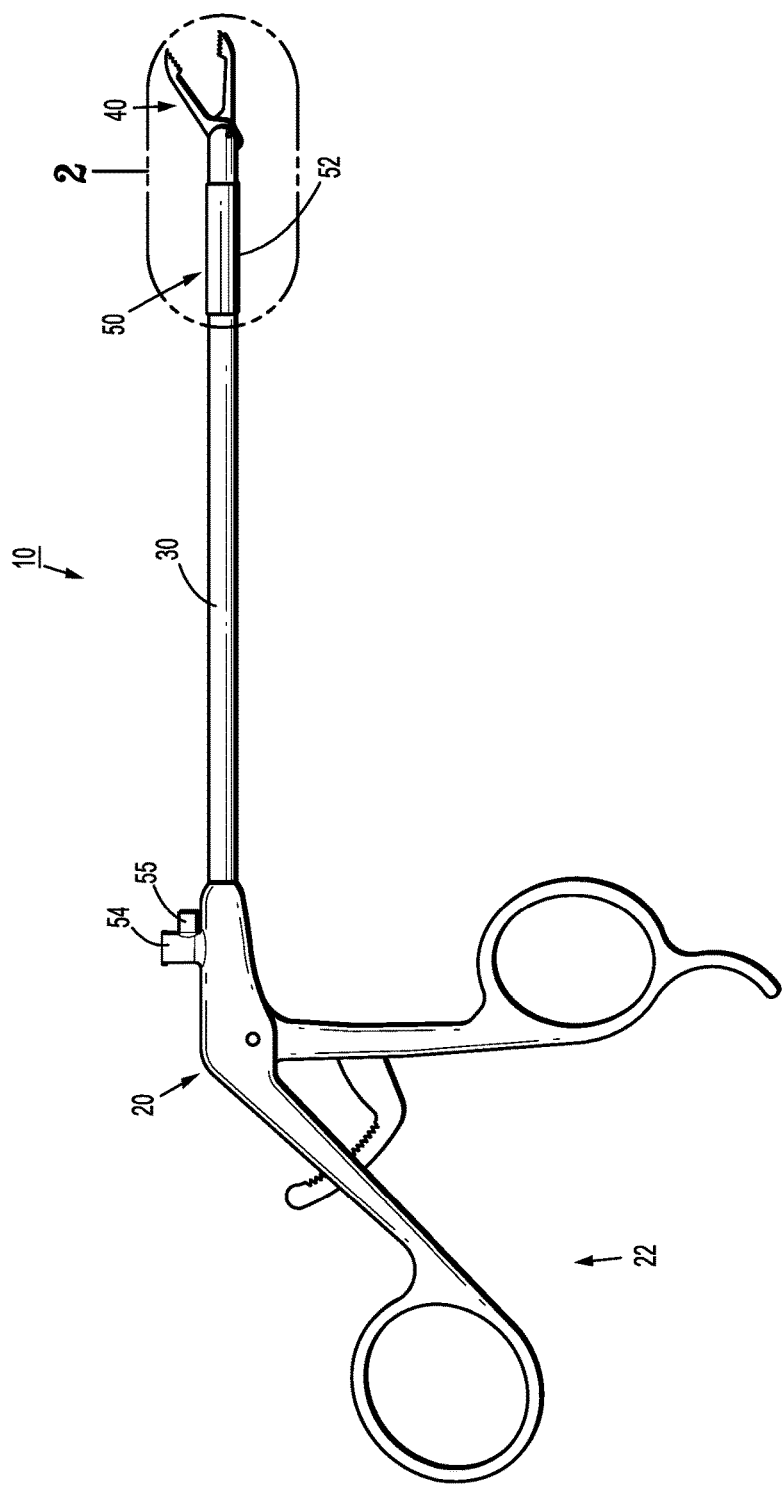
FIG. 1 is a side view of a surgical instrument in accordance with the present disclosure with a blunt dissecting element in a contracted configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. As used herein, the term "dissection" refers generally to "blunt dissection" (i.e., the separation of tissue along existing seams or natural planes in an atraumatic manner) and/or "sharp dissection" (i.e., the separation of tissue by cutting seamless tissue).

During a surgical procedure it may be necessary to dissect tissue to access underlying organs and/or to create space necessary to perform a surgical procedure. This disclosure generally relates to surgical instruments having the capability of effecting blunt tissue dissection and sharp tissue dissection. In embodiments, the surgical instrument includes a blunt tissue dissector and a sharp tissue dissector. The blunt tissue dissector can be secured to an elongated body of the surgical instrument and expanded to effect blunt tissue dissection of tissue surrounding the elongated body of the surgical instrument. In embodiments, a sharp tissue dissector is supported on a distal end of the elongated body and operable independently of the blunt tissue dissector to effect sharp tissue dissection. In embodiments, the blunt tissue dissector can take the form of an expandable device such as a balloon. Alternately, other expandable devices including shape memory expandable devices, mechanically expandable devices, or bands can be used to perform blunt dissection.

Referring to FIG. 1, a surgical instrument 10 is provided in accordance with the present disclosure and includes a housing 20, an elongated body 30, an end effector 40, and a blunt dissection dissector 50. The housing 20 includes a handle assembly 22 for actuating the end effector 40. The elongated body 30 extends from the housing 20 and supports the end effector 40 at a distal end 34 thereof. The end effector 40, shown in a closed position, is configured to manipulate and/or effect sharp dissection of tissue during a surgical procedure.

Figure 2:
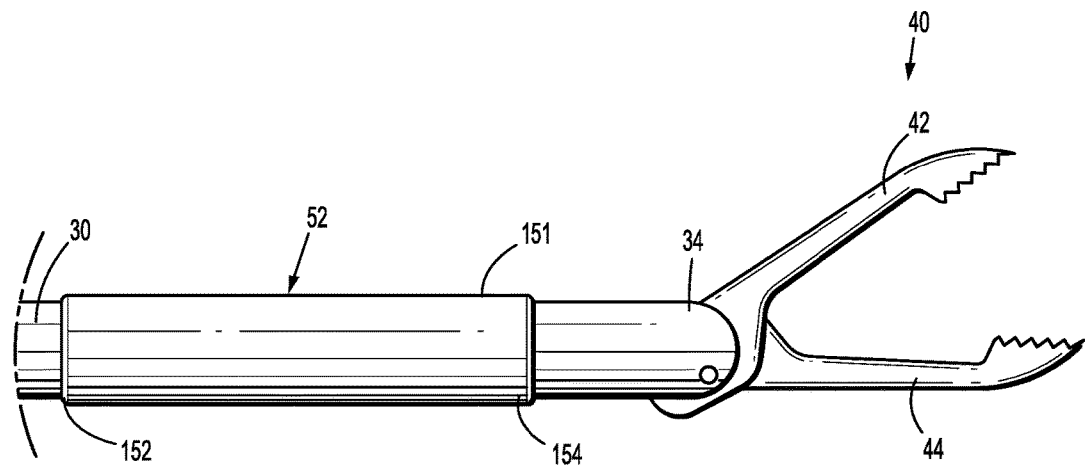
FIG. 2 is an enlarged view of the indicated area of detail of FIG. 1.

With additional reference to FIG. 2, the end effector 40 can include a grasper having first and second jaw members 42, 44 moveable relative to one another to grasp tissue therebetween. In embodiments, a distal end of the first and second jaw members 42, 44 may be configured to atraumatically grasp tissue and a portion of each of the first and second jaw member 42, 44 may be configured to cut/dissect tissue. For the purposes of this disclosure, the end effector 40 is a grasper/sharp tissue dissector. However, it is contemplated that the end effector 40 may include a linear stapler, an annular stapler, an ultrasonic instrument, an electrosurgical instrument, any combination thereof, etc.

Figure 3:
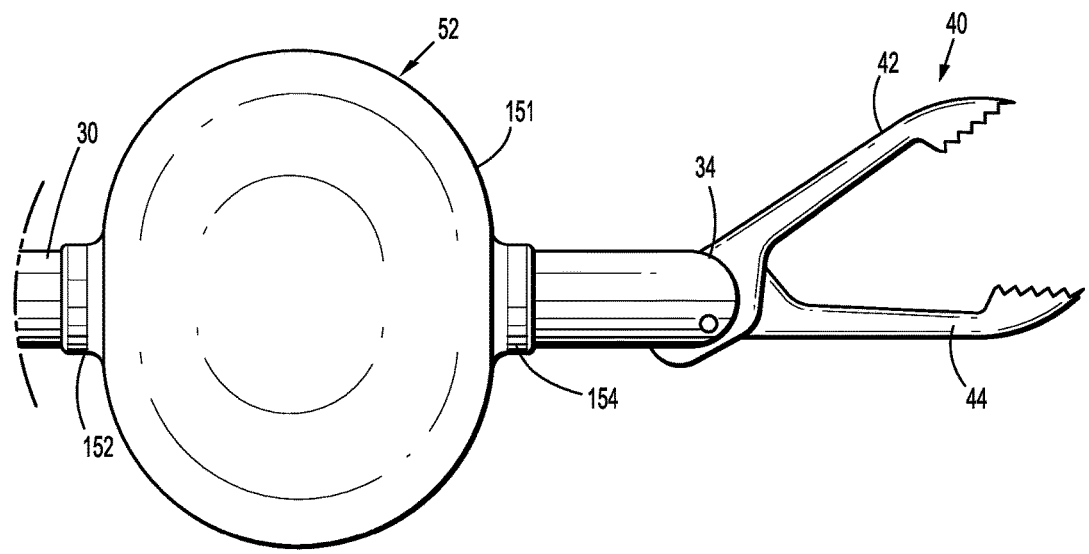
FIG. 3 is a side view of the dissecting element of FIG. 2 in an extended configuration.

Referring now to FIGS. 2 and 3, the blunt dissector 50 includes a dissection element 52 that is secured about the elongated body 30 adjacent to the distal end 34 thereof. In embodiments, the dissection element 52 includes an expandable balloon having a proximal cuff 152, a distal cuff 154, and a dissection wall 151 between the proximal and distal cuffs 152, 154. The distal cuff 154 is positioned adjacent the distal end 34 of the elongated body 30 and the proximal cuff 152 is spaced proximally from the distal cuff 154. The dissection element 52 is movable from a contracted configuration to an expanded configuration. In the contracted configuration (FIG. 2), the dissection element 52 defines a first outer dimension that is substantially similar to or less than an outer diameter of the elongated body 30. In the contracted configuration, the dissection wall 151 is substantially linear and parallel to a longitudinal axis of the elongated body 30. In the expanded configuration (FIG. 3), the dissection element 52 defines a second dimension larger than the outer diameter of the elongated body 30. In embodiments, the dissection wall 151 of the dissection element 52 is arcuate and configured to dissect tissue adjacent or surrounding the elongated body 30 in the expanded configuration. As shown, each of the proximal and distal cuffs 152, 154 is longitudinally fixed about the elongated body 30; however, one or both of the proximal and distal cuffs 152, 154 may slide along the elongated body 30 as the dissection element 52 transitions between the contracted and expanded configurations.

It is envisioned that the blunt dissector 50 can include expandable devices other than balloons. For example, the blunt dissector can include deformable or shape memory bands that can bow outwardly from a contracted configuration to an expanded configuration.

Figure 4:
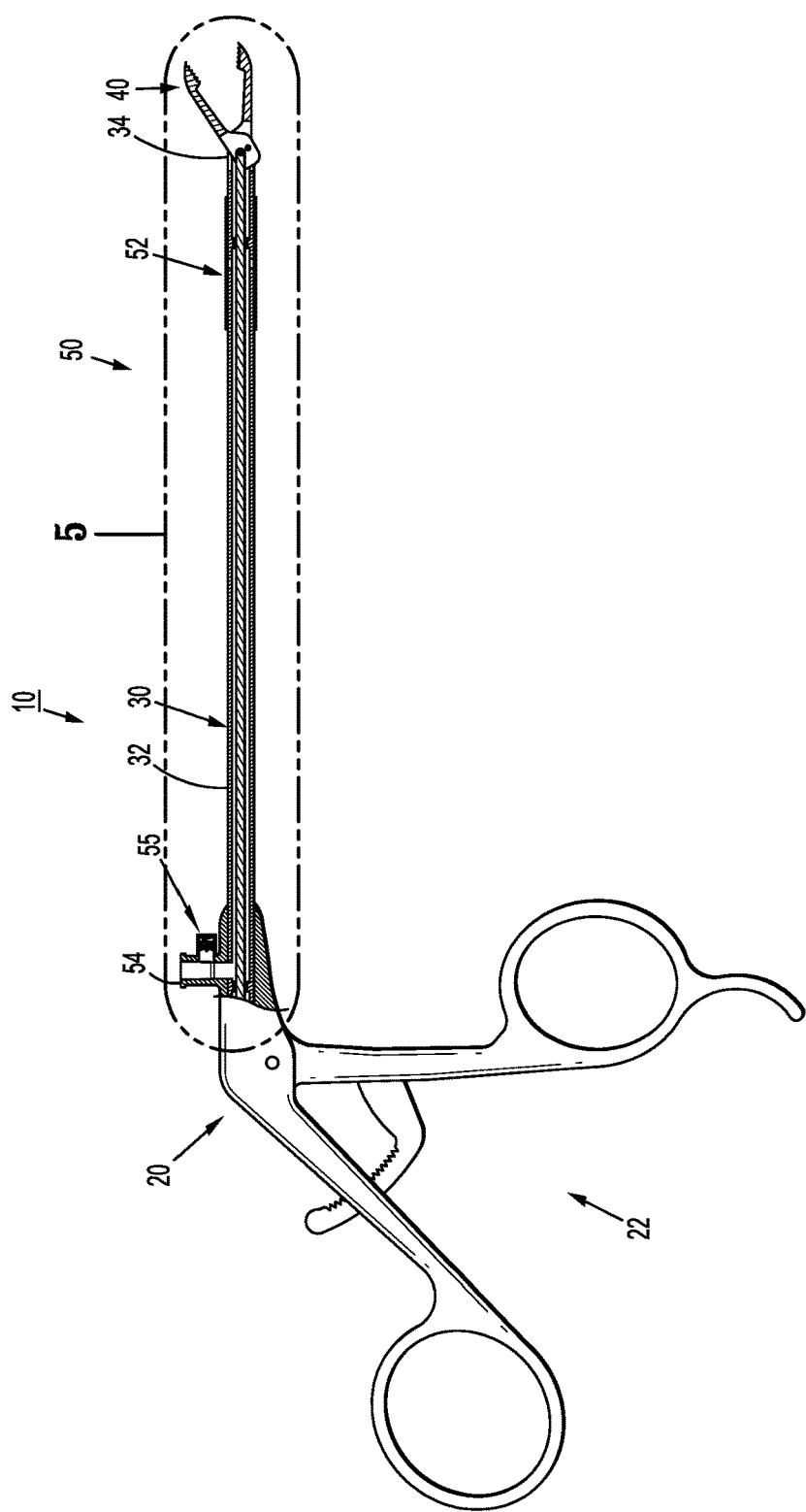
FIG. 4 is a partial side, cross-sectional view of the surgical instrument of FIG. 1.
Figure 5:
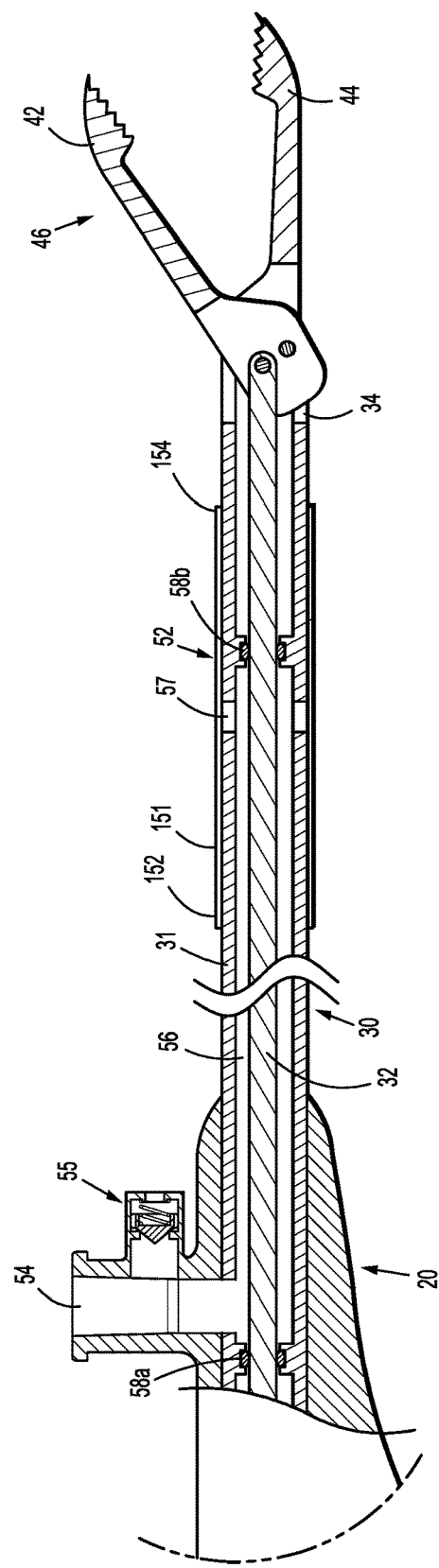
FIG. 5 is an enlarged view of the indicated area of detail of FIG. 4 with the dissecting element in the contracted configuration.
Figure 6:
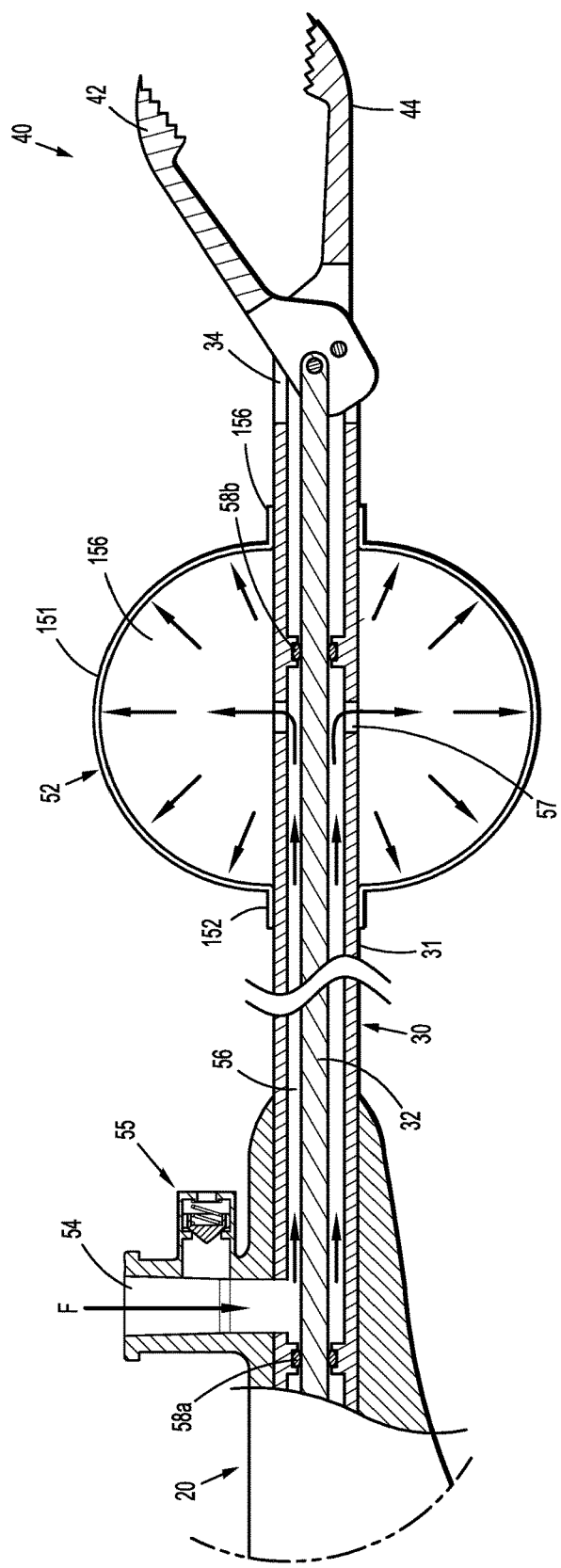
FIG. 6 is a side view of the dissecting element of FIG. 5 in an expended configuration.

Referring to FIGS. 4-6, the housing 20 includes an inflation port 54 that communicates with an inflation channel 56 defined by an outer wall 31 of the elongated body 30. The inflation port 54 is in fluid communication with an interior 156 (FIG. 6) of the dissection element 52 via the inflation channel 56. In embodiments, the elongated body 30 defines inflation openings 57 defined through the outer wall 31 to fluidly connect the inflation channel 56 with the interior 156 of the dissection element 52. The inflation openings 57 are positioned between the proximal and distal cuffs 152, 154 of the dissection element 52. In embodiments, the inflation channel 56 may surround a drive rod 32 that extends through the elongated body 30 to actuate the end effector 40 in response to manipulation of the handle assembly 22. In some embodiments, proximal and distal seals 58a, 58b are positioned within the inflation channel 56 to form a seal about proximal and distal ends of the drive rod 32 such that fluid injected through the inflation port 54 passes through the inflation channel 56 and into the interior 156 of the dissection element 52. It will be appreciated that the proximal seal 58a is positioned proximal to the inflation port 54 and the distal seal 58b is positioned distal to the inflation openings 57.

With particular reference to FIGS. 5 and 6, in the contracted configuration of the dissection element 52, the dissection wall 151 of the dissection element 52 is substantially coplanar with the outer wall 31 of the elongated body 30. As inflation fluid is injected through the inflation port 54, as represented by Arrows F in FIG. 6, the inflation fluid flows through the inflation channel 56 and the inflation openings 57 into the interior 156 of the dissection element 52. As the inflation fluid flows into the interior 156 of the dissection element 52, pressure inside the interior 156 of the dissection element 52 increases such that the dissection wall 151 of the dissection element 52 expands as the dissection element 52 resiliently transitions from the contracted configuration to the expanded configuration. As discussed above, in the expanded configuration of the dissection element 52, the dissection wall 151 is positioned away from the outer wall 31 of the elongated body 30 to dissect tissue surrounding the elongated body 30.

The dissection element 52 is returned to the contracted configuration by withdrawing the inflation fluid from the interior 156 of the dissection element 52 through the inflation port 54. The dissection wall 151 of the dissection element 52 may be biased towards the deflated configuration such that when the inflation fluid is withdrawn from the interior 156 or a discharge gas valve communicating with the interior 156 is opened, the dissection wall 151 will return to the contracted configuration. Additionally or alternatively, when the inflation fluid is withdrawn through the inflation port 54 a vacuum may be applied to the interior 156 of the dissection element 52 via the inflation port 54 to draw the dissection wall 151 into the contracted configuration. It is also contemplated that in embodiments where one of the proximal or distal cuffs 152, 154 is slidable along the elongated body 30, the slidable cuff, e.g., proximal cuff 152, may be biased away from the fixed cuff, e.g., distal cuff 154, such that the dissection wall 151 is biased towards the deflated configuration. It is also contemplated that the inflation portion 54 may include a release valve 55 that is selectively openable such that the inflation fluid may be released to the environment through the release valve 55 to decrease pressure within the interior 156 of the dissection element 52. The release valve 55 may also function as a relief valve to prevent the pressure within the interior 156 of the dissection element 52 from exceeding a predetermined pressure limit. Finally, it is also envisioned that the resilient material defining the dissection element 52 may urge the dissection element 52 to the contracted configuration as described in further detail below.

The dissection element 52 may be a resilient balloon that is inflated by an injection fluid selected from air, nitrogen, oxygen, saline, or any other suitable fluid. It will be appreciated that the injection fluid may be a biocompatible or bioabsorbable fluid such that a release of the injection fluid within a body cavity of a patient will not harm a patient. The dissection wall 151 of the dissection element 52 may be constructed of a resilient biocompatible polymer, a resilient biocompatible rubber, or another suitable biocompatible material such that the dissection element 52 resiliently transitions from the contracted configuration to the expanded configuration and returns to the contracted configuration when the inflation fluid is withdrawn or the release valve 55 is opened to release inflation fluid from the interior 156 of the dissection element 52. The dissection wall 151 may expand such that as the dissection element 52 transitions from the contracted configuration to the expanded configuration, a length of the dissection wall 151 between the proximal cuff 152 and the distal cuff 154 taken along a surface of the dissection wall 151 increases as shown between FIGS. 5 and 6. Alternatively, the length of the dissection wall 151 may be substantially constant such that as the dissection wall 151 transitions from the deflated configuration to the inflated configuration, a slidable cuff, e.g., proximal cuff 152, slides towards a fixed cuff, e.g., distal cuff 154, such that the dissection wall 151 expands without increasing its length.

As shown, the dissection element 52 is substantially spherical in shape when in the inflated configuration; however, it is contemplated that the dissection element 52 may be adapted to be substantially planar in one cross-section and elliptical or substantially circular in another perpendicular cross-section. Additionally or alternatively, the interior 156 of the dissection element 52 may be segmented into two or more bladders which are independently inflatable from one another through the inflation port 54. Examples of such shaped, segmented, and multiple bladder dissection elements are disclosed in U.S. Pat. Nos. 6,758,853, 7,695,487, and 8,540,745. The entire contents of each of these disclosures are incorporated herein by reference.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:
1. A surgical instrument comprising:
a housing having a handle assembly;
an elongated body extending from the housing;
an end effector supported at a distal end of the elongated body, the end effector operably associated with the handle assembly; and
a dissection element having an expanded configuration and a retracted configuration, the dissection element disposed about the elongated body proximal to the distal end of the elongated body and configured to bluntly dissect tissue surrounding the elongated body, the dissection element including a proximal cuff and a distal cuff, the distal cuff disposed about the elongated body adjacent the distal end of the elongated body, the proximal cuff disposed about the elongated body proximal of the distal cuff, at least one of the proximal or distal cuffs configured to translate along the elongated body as the dissection element transitions between the contracted configuration and the expanded configuration.

2. The surgical instrument according to claim 1, wherein the dissection element includes a dissection wall between the proximal and distal cuffs.

3. The surgical instrument according to claim 2, wherein one of the proximal cuff or the distal cuff is longitudinally fixed to the elongated body.

4. The surgical instrument according to claim 2, wherein in the expanded configuration the dissection wall of the dissection element is arcuate between the proximal and distal cuffs.

5. The surgical instrument according to claim 1, wherein in the contracted configuration the dissection wall of the dissection element is substantially linear.

6. The surgical instrument according to claim 5, wherein in the contracted configuration the dissection wall is coplanar with an outer wall of the elongated body.

7. The surgical instrument according to claim 1, wherein the housing includes an inflation port that is in fluid communication with an interior of the dissection element.

8. The surgical instrument according to claim 7, wherein an outer wall of the elongated body defines an inflation channel and an inflation opening that fluidly connect the inflation port and the interior of the dissection element.

9. The surgical instrument according to claim 7, wherein the inflation port includes a release valve that is configured to release inflation fluid from the interior of the dissection element.

10. The surgical instrument according to claim 8, further comprising a drive rod passing through the inflation channel of the elongated body to operably couple the handle assembly to the end effector.

11. The surgical instrument according to claim 10, wherein the elongated body includes a proximal seal and a distal seal positioned about the drive rod to seal the inflation channel.

12. The surgical instrument according to claim 1, wherein the end effector includes a first jaw member and a second jaw member moveable relative to one another.

13. The surgical instrument according to claim 12, wherein the first or second jaw member define a sharp tissue dissector.

14. The surgical instrument according to claim 12, wherein the first and second jaw members include a grasping and a cutting function.

15. The surgical instrument according to claim 1, wherein the dissection element is a balloon.

16. A method of treating tissue, the method comprising:
inserting a surgical instrument through an opening in a body cavity of a patient to access a surgical site;
positioning a dissection element of the surgical instrument adjacent tissue to be dissected;
expanding the dissection element to bluntly dissect tissue adjacent the surgical instrument such that at least one of the proximal or distal cuffs translates along the elongated body;
contracting the dissection element such that the at least one of the proximal or distal cuffs translates along the elongated body; and
treating targeted tissue with an end effector of the surgical instrument positioned distal to the dissection element.

17. The method according to claim 16, wherein treating targeted tissue with the end effector of the surgical instrument includes sharp dissection of the targeted tissue.

18. The method according to claim 16, wherein expanding the dissection element includes injecting fluid through an injection port disposed on a housing of the surgical instrument such that the fluid increases pressure within an interior of the dissection element.

19. The method according to claim 16, wherein contracting the dissection element includes removing fluid through an injection port disposed on a housing of the surgical instrument such that the fluid decreases pressure within an interior of the dissection element.

20. The method according to claim 16, wherein expanding the dissection element to bluntly dissect tissue adjacent the surgical instrument includes the distal cuff translating proximally along the elongated body and wherein contracting the dissection element includes the distal cuff translating distally along the elongated body.

* * * * *